United States Patent
Lynch

(10) Patent No.: US 12,036,017 B2
(45) Date of Patent: Jul. 16, 2024

(54) WEARABLE ASSEMBLY COMPRISING A WEARABLE ARTICLE AND AN ELECTRONICS MODULE ARRANGED TO BE REMOVABLY COUPLED TO THE WEARABLE ARTICLE

(71) Applicant: Prevayl Innovations Limited, Manchester (GB)

(72) Inventor: Michael John Lynch, Cheshire (GB)

(73) Assignee: Prevayl Innovations Limited, Manchester (GB)

( * ) Notice: Subject to any disclaimer, the term of this patent is extended or adjusted under 35 U.S.C. 154(b) by 0 days.

(21) Appl. No.: 17/796,845

(22) PCT Filed: Feb. 9, 2021

(86) PCT No.: PCT/GB2021/050284
§ 371 (c)(1),
(2) Date: Aug. 1, 2022

(87) PCT Pub. No.: WO2021/160997
PCT Pub. Date: Aug. 19, 2021

(65) Prior Publication Data
US 2022/0400980 A1    Dec. 22, 2022

(30) Foreign Application Priority Data

Feb. 10, 2020    (GB) ...................................... 2001799

(51) Int. Cl.
*A61B 5/113*    (2006.01)
*A61B 5/00*    (2006.01)
(Continued)

(52) U.S. Cl.
CPC ........ *A61B 5/1118* (2013.01); *A61B 5/02438* (2013.01); *A61B 5/6805* (2013.01); *A61B 5/742* (2013.01); *A61B 2560/045* (2013.01)

(58) Field of Classification Search
CPC ............................ A61B 5/1118; A61B 5/6804
See application file for complete search history.

(56) References Cited

U.S. PATENT DOCUMENTS

| 9,554,721 B1 | 1/2017 | Zikov |
| 9,619,660 B1 * | 4/2017 | Felix ................... G06F 21/6218 |

(Continued)

FOREIGN PATENT DOCUMENTS

| CN | 204351118 | 5/2015 |
| CN | 206166913 | 5/2017 |

(Continued)

OTHER PUBLICATIONS

International Search Report received in PCT/GB2021/051489 mailed Sep. 20, 2021.

(Continued)

*Primary Examiner* — Michael J D'Abreu
(74) *Attorney, Agent, or Firm* — Suzannah K. Sundby, Esq.; Canady + Lortz LLP

(57) ABSTRACT

The wearable article comprises a sensing component. The electronics module (100) comprises an (interface 109) arranged to couple with the sensing component to receive signals. A processor (101) of the module (100) is configured to process the signals. The signals relate to the activity of a user wearing the wearable article. The processor (101) is configured to process the signals to determine whether the activity of the user is within a predetermined allowable range. A light source (103) of the module (100) is configured to emit light based on the determination by the processor (101). The emitted light indicates whether the activity of the user is within the predetermined allowable range. The electronics module (100) also comprises a housing. The processor (101) and light source (103) are provided in the housing. The housing is constructed such that light emitted by the (Continued)

light source (103) is visible from the outside surface of the housing.

21 Claims, 8 Drawing Sheets

(51) Int. Cl.
*A61B 5/024* (2006.01)
*A61B 5/11* (2006.01)

(56) References Cited

U.S. PATENT DOCUMENTS

| | | |
|---|---|---|
| 10,499,849 B1 | 12/2019 | Chuang |
| 2004/0171956 A1 | 9/2004 | Babashan |
| 2007/0208233 A1 | 9/2007 | Kovacs |
| 2008/0125288 A1 | 5/2008 | Case |
| 2008/0218310 A1 | 9/2008 | Alten |
| 2009/0030333 A1 | 1/2009 | McDonough |
| 2009/0069702 A1 | 3/2009 | How |
| 2009/0112072 A1 | 4/2009 | Banet |
| 2009/0192823 A1 | 7/2009 | Hawkins |
| 2010/0280331 A1 | 11/2010 | Kaufman |
| 2010/0292050 A1 | 11/2010 | Dibenedetto |
| 2010/0292599 A1 | 11/2010 | Oleson |
| 2011/0062237 A1 | 3/2011 | Chaves |
| 2012/0146784 A1 | 6/2012 | Hines |
| 2012/0235821 A1 | 9/2012 | Dibenedetto |
| 2012/0246795 A1 | 10/2012 | Scheffler |
| 2012/0306643 A1 | 12/2012 | Dugan |
| 2013/0120106 A1 | 5/2013 | Cauwels |
| 2013/0175334 A1 | 7/2013 | Miller |
| 2014/0040626 A1 | 2/2014 | Dan |
| 2014/0070957 A1* | 3/2014 | Longinotti-Buitoni ...................... A61B 5/02055 340/870.01 |
| 2014/0135644 A1 | 5/2014 | Kim |
| 2014/0221855 A1 | 8/2014 | McCaffrey |
| 2014/0275876 A1 | 9/2014 | Hansen |
| 2014/0288436 A1 | 9/2014 | Venkatraman |
| 2014/0318699 A1 | 10/2014 | Longinotti-Buitoni |
| 2014/0323827 A1 | 10/2014 | Ahmed |
| 2015/0039042 A1* | 2/2015 | Amsler .................. A61B 90/98 607/7 |
| 2015/0061889 A1 | 3/2015 | Kotaki |
| 2015/0061891 A1 | 3/2015 | Oleson |
| 2015/0081169 A1 | 3/2015 | Pisz |
| 2015/0088002 A1 | 3/2015 | Podhajsky |
| 2015/0099991 A1 | 4/2015 | Yamaguchi |
| 2015/0182841 A1 | 7/2015 | Martikka |
| 2015/0230752 A1 | 8/2015 | Fort |
| 2015/0231481 A1 | 8/2015 | Jones |
| 2015/0305674 A1 | 10/2015 | McPherson |
| 2016/0058313 A1 | 3/2016 | Sato |
| 2016/0098581 A1 | 4/2016 | Marti Ascencio |
| 2016/0120460 A1 | 5/2016 | Eom |
| 2016/0134642 A1 | 5/2016 | Hamid |
| 2016/0135516 A1 | 5/2016 | Cobbett |
| 2016/0159106 A1 | 6/2016 | De Castro |
| 2016/0192716 A1 | 7/2016 | Lee |
| 2016/0256104 A1 | 9/2016 | Romem |
| 2016/0371438 A1 | 12/2016 | Annulis |
| 2016/0374588 A1 | 12/2016 | Shariff |
| 2017/0007129 A1* | 1/2017 | Kaib .................. A61N 1/3904 |
| 2017/0031435 A1 | 2/2017 | Raffle |
| 2017/0071548 A1 | 3/2017 | Wiebe |
| 2017/0086519 A1 | 3/2017 | Vigano' |
| 2017/0094216 A1 | 3/2017 | Ekambaram |
| 2017/0140120 A1 | 5/2017 | Thrower |
| 2017/0181703 A1 | 6/2017 | Kaib |
| 2017/0196513 A1 | 7/2017 | Longinotti-Buitoni |
| 2017/0243615 A1 | 8/2017 | Tabak |
| 2017/0303864 A1 | 10/2017 | Su |
| 2017/0332946 A1 | 11/2017 | Kikkeri |
| 2017/0368413 A1 | 12/2017 | Shavit |
| 2018/0092698 A1 | 4/2018 | Chopra |
| 2018/0174683 A1 | 6/2018 | Franz |
| 2018/0228406 A1 | 8/2018 | Mendelsohn |
| 2018/0232925 A1 | 8/2018 | Frakes |
| 2018/0300919 A1 | 10/2018 | Muhsin |
| 2018/0345079 A1 | 12/2018 | Lindman |
| 2018/0353152 A1 | 12/2018 | Teji |
| 2018/0358119 A1 | 12/2018 | Bhushan |
| 2019/0000384 A1 | 1/2019 | Gupta |
| 2019/0037932 A1 | 2/2019 | Martin |
| 2019/0053469 A1 | 2/2019 | Mardirossian |
| 2019/0090765 A1 | 3/2019 | Cuccinello |
| 2019/0196411 A1 | 6/2019 | Yuen |
| 2019/0246734 A1 | 8/2019 | Nurse |
| 2020/0333837 A1 | 10/2020 | Weiner |
| 2020/0367758 A1 | 11/2020 | Kimura |
| 2022/0101994 A1 | 3/2022 | Crofts |
| 2022/0142572 A1 | 5/2022 | Crofts |
| 2023/0115286 A1 | 4/2023 | Crofts |

FOREIGN PATENT DOCUMENTS

| | | |
|---|---|---|
| CN | 208624750 | 3/2019 |
| CN | 110584627 | 12/2019 |
| CN | 209928492 | 1/2020 |
| CN | 111035376 | 4/2020 |
| EP | 3431146 | 1/2019 |
| GB | 2476690 | 7/2011 |
| GB | 2561575 | 10/2018 |
| GB | 2563065 | 12/2018 |
| GB | 2565330 | 2/2019 |
| GB | 2567533 | 4/2019 |
| GB | 2586950 | 3/2021 |
| GB | 2590986 | 7/2021 |
| GB | 2591819 | 8/2021 |
| GB | 2593433 | 9/2021 |
| GB | 2593434 | 9/2021 |
| GB | 2596157 | 12/2021 |
| GB | 2596158 | 12/2021 |
| GB | 2596782 | 1/2022 |
| GB | 2596783 | 1/2022 |
| GB | 2590985 | 4/2022 |
| JP | 2015073807 | 4/2015 |
| KR | 101907383 | 10/2018 |
| WO | 0004522 | 1/2000 |
| WO | 2006009830 | 1/2006 |
| WO | 2008038141 | 4/2008 |
| WO | 2012167026 | 12/2012 |
| WO | 2014192002 | 12/2014 |
| WO | 2015056262 | 4/2015 |
| WO | 2017198978 | 11/2017 |
| WO | 2018134432 | 7/2018 |
| WO | 2018145719 | 8/2018 |
| WO | 2018152475 | 8/2018 |
| WO | 2019086908 | 5/2019 |
| WO | 2019104374 | 6/2019 |

OTHER PUBLICATIONS

Written Opinion received in PCT/GB2021/051489 mailed Sep. 20, 2021.
"EMGlare Heart", available from https://emglare.com/ by at least Aug. 20, 2021, , Publisher: emglare.com [online].
"Enflux Exercise Clothing: Improve Form! Real-time Analysis", https://www.kickstarter.com/projects/1850884998/enflux-smart-clothing-3d-workout-tracking-and-form/description, Mar. 1, 2017, Publisher: Enflux exercise clothing, kickstarter.com, [online].
Examination Report received in GB1908181.9 mailed Mar. 16, 2020.
Examination Report received in GB1908181.9 mailed Apr. 16, 2021.
Search Report received in GB1908181.9 mailed Dec. 9, 2019.
Examination Report received in GB1908187.6 mailed May 29, 2020.
Search and Examination Report received in GB1908187.6 mailed Dec. 12, 2019.

(56) References Cited

OTHER PUBLICATIONS

Lightbody et al., A versatile high-performance visual fiducial marker detection system with scalable identity encoding, Apr. 3, 2017, pp. 276-282, Publisher: Proceedings of the Symposium on Applied Computing.
https://nakedlabs.com/naked-home-body-scanner, Publisher: Naked Labs available at least by Oct. 4, 2018.
"QR Code & Bluetooth Connection Tutorial with Shimmer", https://www.youtube.com/watch?v=I6pZLr2h9ag, , Page(s) (screenshot provided), Publisher: YouTube video purportedly uploaded by Shimmer Sensing on Feb. 6, 2014.
Prosecution in U.S. Appl. No. 17/432,583.
Prosecution in U.S. Appl. No. 17/432,586.
Prosecution in U.S. Appl. No. 17/999,972.
Prosecution in U.S. Appl. No. 18/081,016.
International Search Report received in PCT/GB2020/051360 mailed Aug. 20, 2020.
Written Opinion received in PCT/GB2020/051360 mailed Aug. 20, 2020.
International Search Report received in PCT/GB2020/051361 mailed Aug. 4, 2020.
Written Opinion received in PCT/GB2020/051361 mailed Aug. 4, 2020.
International Search Report received in PCT/GB2021/050284 mailed Apr. 12, 2021.
Written Opinion received in PCT/GB2021/050284 mailed Apr. 12, 2021.
Prosecution history of GB2590985, granted Mar. 15, 2022.

\* cited by examiner

WEARABLE ASSEMBLY COMPRISING A WEARABLE ARTICLE AND AN ELECTRONICS MODULE ARRANGED TO BE REMOVABLY COUPLED TO THE WEARABLE ARTICLE

The present invention is directed towards a wearable assembly and, in particular, a wearable assembly arranged to generate an output based on a determined activity level of a user wearing the assembly.

BACKGROUND

Wearable articles can be designed to interface with a wearer of the article, and to determine information such as the wearer's heart rate, rate of respiration, activity level, and body positioning. Such properties can be measured with a sensor assembly that includes a sensor for signal transduction and/or microprocessors for analysis. Wearable articles have electrically conductive pathways to allow for signal transmission between an electronics module for processing and communication and sensing components. The wearable articles may be garments. Such garments which are commonly referred to as 'smart clothing' and may also be referred to as 'biosensing garments' if they measure biosignals. Typically, different types of garments may have different sensors.

It is desirable to provide a system which overcomes at least some of the problems associated with the prior art, whether explicitly discussed herein or otherwise.

SUMMARY

According to the present disclosure there is provided an electronics arrangement, wearable article, and method as set forth in the appended claims. Other features of the invention will be apparent from the dependent claims, and the description which follows.

According to a first aspect of the disclosure, there is provided an electronics arrangement for a wearable article. The electronics arrangement comprises a processor configured to process signals sensed by a sensing component. The signals relate to the activity of a user wearing the wearable article. The processor is configured to process the signals so as to determine whether the activity of the user is within a predetermined allowable range. The electronics arrangement comprises a light source configured to emit light based on the determination by the processor. The emitted light is for indicating whether the activity of the user is within the predetermined allowable range.

Advantageously, the electronics arrangement is able to generate a visual output which indicates whether the activity of the user is within the predetermined allowable range. This allows the user wearing the garment or another person to quickly ascertain the status of the user such as whether they are in the correct training zone or fat burning zone during cardio exercise.

The electronics arrangement may comprise an electronics module. The processor and light source may be components of the electronics module. The electronics module may further comprise a housing. The processor and/or the light source may be provided in the housing of the electronics module. The housing may be constructed such that light emitted by the light source is visible from the outside surface of the housing.

The electronics arrangement may be arranged to be removably attached to the wearable article.

The electronics arrangement may comprise the sensing component. The sensing component may be provided in an electronics module with the processor and/or the light source. The sensing component may be separate to the processor and/or the light source. The sensing component may be incorporated into the wearable article.

The electronics arrangement may further comprise an interface element arranged to communicatively couple with a sensing component of the wearable article so as to receive signals from the sensing component.

The electronics arrangement may further comprise an input unit configured to receive a user input for selecting an operational mode. The processor may be configured to process the signals so as to determine whether the activity of the user is within a predetermined allowable range for the selected operational mode.

The input unit may comprise a sensor arranged to detect an object being brought into proximity with the electronics arrangement. The sensor may be a motion sensor. The motion sensor may comprise an accelerometer. The processor may be configured to process signals received from the motion sensor so as to determine whether the activity of the user is within the predetermined allowable range.

The light source may be configured to emit light having a first property when the activity of the user is determined to be within the predetermined allowable range. The light source may be configured to emit light having a property other than the first property when the activity of the user is determined to be outside of the predetermined allowable range.

The light source may be configured to emit light having a second property when the activity of the user is determined to be outside of the predetermined allowable range but within a predetermined distance of the allowable range. The light source may be configured to emit light having a third property when the activity of the user is outside of the predetermined allowable range and more than the predetermined distance from the predetermined allowable range.

The light source may be configured to emit light having a first colour when the activity of the user is determined to be within the predetermined allowable range. The light source may be configured to emit light having a colour other than the first colour when the activity of the user is determined to be outside of the predetermined allowable range.

The electronics arrangement may further comprise an interface element arranged to communicatively couple with a sensing component of the wearable article so as to receive signals from the sensing component.

The electronics arrangement may further comprise a communicator arranged to communicatively couple with an external device so as to send data to and/or receive data from the external device.

The electronics arrangement may be provided with a surface which increases friction between the wearable article and the electronics arrangement so as to limit motion of the electronics arrangement relative to the wearable article.

The light source may comprise one or a plurality of light emitting diodes (LEDs).

According to a second aspect of the disclosure, there is provided a wearable assembly comprising a wearable article and the electronics arrangement of the first aspect of the disclosure.

The wearable article may further comprise a sensing component, and optionally an electrically conductive pathway extending from the sensing component to the electronics module holder.

The wearable article may be constructed such that light emitted by the light source is visible from the outside surface of the wearable article.

The wearable article may comprise an opening positioned such that light emitted by the light source is visible from the outside surface of the wearable article. The wearable article may comprise a window constructed from a transparent, translucent, or light-diffracting material. The wearable article may comprise an open-cell construction in the vicinity of the light source such that the light source is visible from the outside surface of the wearable article.

The wearable article may comprise an electronics module holder arranged to hold an electronics module of the electronics arrangement.

The electronics module holder may comprise a pocket.

The electronics module holder may be provided on an inside surface of the wearable article or an outside surface of the wearable article.

The wearable article may further comprise a visual marker located on an outside surface of the wearable article. The visual marker may be located at a position corresponding to processor and/or the light source of the electronics arrangement. The visual marker may be located at a position corresponding to the electronics module holder. The visual marker may be configured to indicate the location of the electronics module when located in the electronics module holder. The visual marker may be configured to indicate the location of an input unit of the electronics arrangement/electronics module such that an object tapping on the wearable article in the vicinity of the visual marker is detectable by the input unit of the electronics module.

The visual marker may comprise a machine-readable code, optionally wherein the machine-readable code is a QR code.

The inner surface of the electronics module holder may be provided with a surface which increases friction between the inner surface and the electronics module when positioned within the electronics module holder.

The wearable article may be a garment.

The wearable article may comprise one or more sensing components. The sensing components may be biosensing components. The sensing components may comprise one or more components of a temperature sensor, a humidity sensor, a motion sensor, an electropotential sensor, an electroimpedance sensor, an optical sensor, an acoustic sensor. Here, "component" means that not all of the components of the sensor may be provided in the wearable article. The processing logic, power and other functionality may be provided in the electronics arrangement. The wearable article may only comprise the minimal functionality to perform the sensing such as by only including sensing electrodes. The temperature sensor may be arranged to measure an ambient temperature, a skin temperature of a human or animal body, or a core temperature of a human or animal body. The humidity sensor may be arranged to measure humidity or skin-surface moisture levels for a human or animal body. The motion sensor may comprise one or more of an accelerometer, a gyroscope, and a magnetometer sensor. The motion sensor may comprise an inertial measurement unit. The electropotential sensor may be arranged to perform one or more bioelectrical measurements. The electropotential sensor may comprise one or more of electrocardiography (ECG) sensor modules, electrogastrography (EGG) sensor modules, electroencephalography (EEG) sensor modules, and electromyography (EMG) sensor modules. The electroimpedance sensor may be arranged to perform one or more bioimpedance measurements. Bioimpedance sensors can include one or more of plethysmography sensor modules (e.g., for respiration), body composition sensor modules (e.g., hydration, fat, etc.), and electroimpedance tomography (EIT) sensors. An optical sensor may comprise a photoplethysmography (PPG) sensor module or an orthopantomogram (OPG) sensor module.

According to a third aspect of the disclosure, there is provided a method performed by an electronics arrangement for a wearable article. The method comprises receiving, by a processor of the electronics arrangement, signals sensed by a sensing component, the signals relating to the activity of a user wearing the wearable article. The method comprises processing, by the processor, the signals so as to determine whether the activity of the user is within a predetermined allowable range. The method comprises controlling, by the processor, a light source of the electronics arrangement to emit light based on the determination by the processor, wherein the emitted light is for indicating whether the activity of the user is within the predetermined allowable range.

According to a fourth aspect of the disclosure, there is provided a wearable article comprising an electronics module holder arranged to hold an electronics module comprising a light source, wherein the wearable article is constructed such that light emitted by the light source is visible from the outside surface of the wearable article.

The wearable article may comprise an opening positioned such that light emitted by the light source is visible from the outside surface of the wearable article. The wearable article may comprise a window constructed from a transparent, translucent, or light-diffracting material The wearable article may comprise an open-cell construction in the vicinity of the light source such that the light source is visible from the outside surface of the wearable article.

The electronics module holder may comprise a pocket. The electronics module holder may be provided on an inside surface of the wearable article. The electronics module holder may be provided on an outside surface of the wearable article.

The wearable article may further comprise a sensing component. The wearable article may further comprise an electrically conductive pathway extending from the sensing component to the electronics module holder.

The wearable article may further comprise a visual marker located on an outside surface of the wearable article. The visual marker may be located at a position corresponding to the electronics module holder. The visual marker may be configured to indicate the location of the electronics module when located in the electronics module holder. The visual marker may be configured to indicate the location of electronics component of the electronics module such that an object being brought into the vicinity of the visual marker is detectable by the electronics component of the electronics module. The visual marker comprises a machine-readable code. The machine-readable code may comprise a QR code.

The inner surface of the electronics module holder may be provided with a surface which increases friction between the inner surface and the electronics module when positioned within the electronics module holder.

The wearable article may be a garment.

The wearable article may comprise an electronics module. The electronics module may comprise a processor configured to process signals sensed by a sensing component; and a light source configured to emit light under the control of the processor. The electronics module holder of the wearable article is arranged to hold the electronics module.

The signals may relate to the activity of a user wearing the wearable article. The processor may be configured to process the signals so as to determine whether the activity of the user is within a predetermined allowable range.

The light source may be configured to emit light based on the determination by the processor, wherein the emitted light is for indicating whether the activity of the user is within the predetermined allowable range.

According to a sixth aspect of the disclosure, there is provided an electronics arrangement for a wearable article. The electronics arrangement comprises a processor configured to process signals sensed by a sensing component, the signals relating to the cardiac activity of a user wearing the wearable article. The processor is configured to process the signals so as to determine whether the cardiac activity of the user is within a predetermined allowable range. The electronics arrangement comprises an output unit configured to generate an output based on the determination by the processor, wherein the output is for indicating whether the activity of the user is within the predetermined allowable range.

The processor may be arranged to determine whether the cardiac activity of the user is within a predetermined heart rate zone, and wherein the output unit may be configured to generate an output having a first property when the user is within the predetermined heart rate zone.

The processor may be arranged to determine whether the cardiac activity of the user is outside of the predetermined heart rate zone. The output unit may be configured to generate an output having a property other than the first property when the user is outside of the predetermined heart rate zone.

The output unit may be configured to generate an output having a second property when the cardiac activity of the user is outside of the predetermined heart rate zone but within a predetermined distance of the predetermined heart rate zone, and wherein the output unit is configured to generate an output having a third property when the activity of the user is outside of the predetermined heart rate zone and more than the predetermined distance of the predetermined heart rate zone.

The output unit may comprise a light source, audio output unit or haptic feedback unit. The haptic feedback unit may be configured to generate an electrical or vibrational impulse. The output unit may be arranged to transmit a signal to an external device such as an external speaker or display for generating the output. The electronics arrangement may comprise some or all of the features of the first aspect of the disclosure. The electronics arrangement may be incorporated into wearable article such as the wearable article of the second aspect of the disclosure.

According to a seventh aspect of the disclosure, there is provided an electronics arrangement for a wearable article. The electronics arrangement comprises a processor configured to process signals sensed by a sensing component, the signals relating to the temperature of a user wearing the wearable article, the processor configured to process the signals so as to determine whether the temperature of the user is within a predetermined allowable range; and an output unit configured to generate an output based on the determination by the processor, wherein the output is for indicating whether the temperature of the user is within the predetermined allowable range.

The processor may be configured to estimate the temperature of the user based on cardiac activity of the user measured by one or more cardiac sensing components. The temperature may be an estimate of the core temperature of the user.

The processor may be arranged to determine whether the temperature of the user is within a predetermined allowable range, and wherein the output unit is configured to generate an output having a first property when the user is within the predetermined allowable range.

The processor may be arranged to determine whether the temperature of the user is outside of the predetermined allowable range, and wherein the output unit is configured to generate an output having a property other than the first property when the user is outside of the predetermined allowable range.

The output unit may be configured to generate an output having a second property when the temperature of the user is outside of the predetermined allowable range but within a predetermined distance of the predetermined allowable range, and wherein the output unit is configured to generate an output having a third property when the temperature of the user is outside of the predetermined allowable range and more than the predetermined distance from the predetermined allowable range.

The output unit may comprise a light source, audio output unit or haptic feedback unit. The haptic feedback unit may be configured to generate an electrical or vibrational impulse. The output unit may be arranged to transmit a signal to an external device such as an external speaker or display for generating the output. The electronics arrangement may comprise some or all of the features of the first aspect of the disclosure. The electronics arrangement may be incorporated into a wearable article such as the wearable article of the second aspect of the disclosure.

According to an eighth aspect of the disclosure, there is provided an electronics arrangement for a wearable article. The electronics arrangement comprises a processor configured to process signals sensed by a sensing component, the signals relating to the hydration level of a user wearing the wearable article, the processor configured to process the signals so as to determine whether the hydration level of the user is within a predetermined allowable range. The electronics arrangement comprises an output unit configured to generate an output based on the determination by the processor, wherein the output is for indicating whether the hydration level of the user is within the predetermined allowable range.

The processor may be arranged to determine whether the hydration level of the user is within a predetermined allowable range, and wherein the output unit is configured to generate an output having a first property when the user is within the predetermined allowable range.

The processor may be arranged to determine whether the hydration level of the user is outside of the predetermined allowable range. The output unit may be configured to generate an output having a property other than the first property when the user is outside of the predetermined allowable range.

The output unit may be configured to generate an output having a second property when the hydration level of the user is outside of the predetermined allowable range but within a predetermined distance of the predetermined allowable range, and wherein the output unit is configured to generate an output having a third property when the hydration level of the user is outside of the predetermined allowable range and more than the predetermined distance from the predetermined allowable range.

The output unit may comprise a light source, audio output unit or haptic feedback unit. The haptic feedback unit may be configured to generate an electrical or vibrational impulse. The output unit may be arranged to transmit a signal to an external device such as an external speaker or display for generating the output. The electronics arrangement may comprise some or all of the features of the first aspect of the disclosure. The electronics arrangement may be incorporated into a wearable article such as the wearable article of the second aspect of the disclosure.

The present disclosure is not limited to wearable articles. The electronics arrangement disclosed herein may be incorporated into other forms of devices such as user electronic devices (e.g. mobile phones). In additions, they may be incorporated into any form of textile article. Textile articles may include upholstery, such as upholstery that may be positioned on pieces of furniture, vehicle seating, as wall or ceiling décor, among other examples.

BRIEF DESCRIPTION OF THE DRAWINGS

Examples of the present disclosure will now be described with reference to the accompanying drawings, in which.

DETAILED DESCRIPTION

Figure 1:
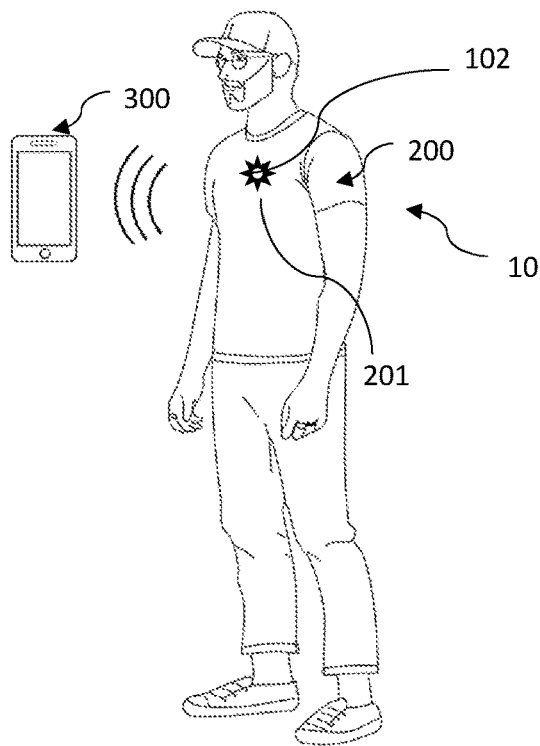
FIG. 1 shows an example system according to aspects of the present disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of electronic device which may be worn by a user such as a smart watch, necklace, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, swimwear, wetsuit or drysuit. The wearable article/garment may be constructed from a woven or a non-woven material. The wearable article/garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment. The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

The following description refers to particular examples of the present disclosure where the wearable article is a garment. It will be appreciated that the present disclosure is not limited to garments and other forms of wearable article are within the scope of the present disclosure as outlined above.

Referring to FIG. 1, there is shown an example system 10 according to aspects of the present disclosure. The system 10 comprises an electronics module 100 (FIG. 2), a garment 200, and a mobile device 300. The garment 200 is worn by a user. The electronics module 100 is attached to the garment 200. The electronics module 100 and garment 200 together form a wearable assembly. The electronics module 100 is provided within the garment 200 and is not visible in FIG. 1.

The electronics module 100 is arranged to integrate with electronic components incorporated into the garment 200 so as to obtain signals from the electronic components. The combination of the electronics module 100 and the electronic components of the garment 200 can be considered as an electronics arrangement according to aspects of the present disclosure. The electronics components of the electronics module 100 can be considered as an electronics arrangement according to aspect of the present disclosure. The electronics arrangement may be distributed components and not be all contained within a housing. The following description refers to particular examples of the present disclosure where the electronics arrangement comprises an electronics module with a housing. will be appreciated that the present disclosure is not limited to electronics modules comprising housings and other forms of electronics arrangements are within the scope of the present disclosure as outlined above. The electronics module may be a standalone device such as a portable electronic device (e.g. a mobile phone).

The electronics components may comprise components of sensors. The electronics components may comprise electrodes. The electronics module 100 is further arranged to wirelessly communicate data to the mobile device 300. Various protocols enable wireless communication between the electronics module 100 and the mobile device 300. Example communication protocols include Bluetooth®, Bluetooth® Low Energy, and near-field communication (NFC).

The electronics module 100 may be removable from the garment 200. The mechanical coupling of the electronic module 100 to the garment 200 may be provided by a mechanical interface such as a clip, a plug and socket arrangement, etc. The mechanical coupling or mechanical interface may be configured to maintain the electronic module 100 in a particular orientation with respect to the garment 200 when the electronic module 100 is coupled to the garment 200. This may be beneficial in ensuring that the electronic module 100 is securely held in place with respect to the garment 200 and/or that any electronic coupling of the electronic module 100 and the garment 200 (or a component of the garment 200) can be optimized. The mechanical coupling may be maintained using friction or using a positively engaging mechanism, for example.

Beneficially, the removable electronic module 100 may contain all of the components required for data transmission and processing such that the garment 200 only comprises the sensor components and communication pathways. In this way, manufacture of the garment 200 may be simplified. In addition, it may be easier to clean a garment 200 which has fewer electronic components attached thereto or incorporated therein. Furthermore, the removable electronic module 100 may be easier to maintain and/or troubleshoot than embedded electronics. The electronic module 100 may comprise flexible electronics such as a flexible printed circuit (FPC). The electronic module 100 may be configured to be electrically coupled to the garment 200.

It may be desirable to avoid direct contact of the electronic module 100 with the wearer's skin while the garment 200 is being worn. It may be desirable to avoid the electronic module 100 coming into contact with sweat or moisture on the wearer's skin or other sources of moisture such as from rain or a shower. The electronic module 100 may be provided with a waterproof coating or waterproof casing. For example, the electronic module 100 may be provided with a silicone casing. It may further be desirable to provide an electronics module holder such as a pocket in the garment to contain the electronic module in order to prevent chafing or rubbing and thereby improve comfort for the wearer. The pocket may be provided with a waterproof lining in order to prevent the electronic module 100 from coming into contact with moisture.

Figure 2:
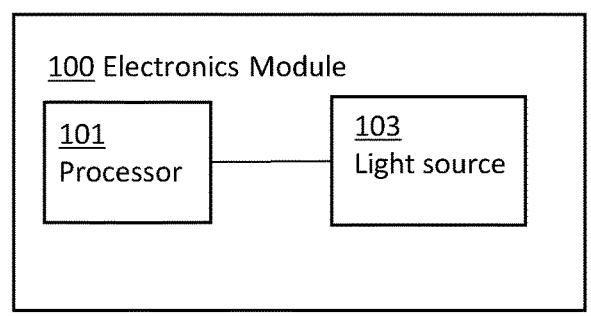
FIG. 2 shows a schematic diagram for an example electronics module according to aspects of the present disclosure.

Referring to FIG. 2, there is shown a simplified schematic diagram of an example electronics module 100 according to aspects of the present disclosure. The electronics module 100 comprises a processor 101 configured to process signals sensed by a sensing component of the electronics module 100 and/or the garment 200. The signals relate to the activity of a user wearing the garment 200. The processor 101 is configured to process the signals so as to determine whether the activity of the user is within a predetermined allowable range. The electronics module 100 comprises a light source 103 configured to emit light based on the determination by the processor 101. The emitted light is for indicating whether the activity of the user is within the predetermined allowable range. The garment 200 is constructed such that the emitted light 102 is visible from the outside surface 201 of the garment 200.

The light source 103 is configured to emit light having a first property when the activity of the user is determined to be within the predetermined allowable range. The first property may comprise one or more of a colour, intensity, pattern, frequency, or switching on/off (the light source 103 may flicker or blink in a particular way) amongst others.

The light source 103 is configured to emit light having a property other than the first property when the activity of the user is determined to be outside of the predetermined allowable range. In some examples, the light source 103 is configured to emit light having a first colour when the activity of the user is determined to be within the predetermined allowable range. In some examples, the light source 103 is configured to emit light having a colour other than the first colour when the activity of the user is determined to be outside of the predetermined allowable range.

In some examples, the light source 103 is configured to emit light having a second property when the activity of the user is determined to be outside of the predetermined allowable range but within a predetermined distance of the allowable range.

In some examples, the light source 103 is configured to emit light having a third property when the activity of the user is outside of the predetermined allowable range and more than the predetermined distance from the predetermined allowable range.

In some examples, the user wearing the garment 200 may desire to undergo exercise while operating in a certain heart rate zone. Heart rate zones are commonly used to indicate levels of exertion during exercise/competition. Heart rate zones are ranges that define the upper and lower limits of training intensities. Heart rate zones are calculated using a predicted maximum heart rate (HRMax) which can be determined based on factors such as the age of the user. Each heart rate one is based on an individual's maximum heart rate (HRMax). There are a number of ways to calculate HRMax. In some examples, HRMax is determined using the formula HRMax=220−(0.7×Age). Age refers to the age of the user in years.

A first heart rate zone, also known as training zone 1, may be defined as 50-60% HRMax. A user may desire to remain in training zone 1 if they are a novice exerciser, exercising for weight management, or recovering from an injury. A second heart-rate zone, also known as training zone 2, may be defined as 60%-70% HRMax. This may be referred to as the fat-burning zone. Training zone 2 is beneficial for increasing aerobic resistance, burning fat, and strengthening body tolerance for higher intensity training. A third heart rate zone, also known as training zone 3, may be defined as 70%-80% HRMax. This may be referred to as the aerobic zone. Training zone 3 is beneficial for enhancing aerobic power and improving blood circulation. A fourth heart rate zone, also known as training zone 4, may be defined as 80%-90% HRMax. This may be referred to as the anaerobic zone. Training zone 4 is beneficial for improving anaerobic tolerance and high speed endurance. A fifth heart rate zone, also known as training zone 5, may be defined as 90%-100% HRMax. This may be referred to as the VO2 max zone and is beneficial for toning the neuromuscular system and increasing maximum sprint race speed.

A user may prefer to remain in a desired heart rate zone (such as the second heart rate zone) during their exercise. The sensing component measures heart rate activity (cardiac activity). The sensing component may comprise one or more ECG electrodes for measuring heart rate activity or other known types of sensing components for measuring heart rate activity. The processor 101 receives the heart rate activity signals and determines from the heart rate activity signals and optionally data from other sensing components, the heart rate zone the user is in. If the processor 101 determines that the user is in the desired heart rate zone, the processor 101 controls the light source 103 to emit light having a first property. The first property may be, for example, green-coloured light. If the processor 101 determines that the user's heart rate activity is just outside of the desired heart rate zone (e.g. within 10% of the desired heart rate zone), the processor 101 controls the light source 103 to emit light having a second property. The second property may be, for example, amber-coloured light. The light source 103 may comprise a plurality of light-emitting diodes (LEDs) so as to emit light having different colours. For example, the light source 103 may comprise a Red Green Blue (RGB) LED package comprising a Red LED, a Green LED, and a Blue LED. If the processor 101 determines that the user's heart rate activity is more than a predetermined distance of the desired heart rate zone (e.g. more than 10% outside of the desired heart rate zone), the processor 101 controls the light source 103 to emit light having a third property. The third property may be, for example, red-coloured light. In this way, the electronics module 100 uses a traffic light system to provide easy to understand feedback about the performance of the user. This feedback may be clearly visible to the user or third party such as team-mate, coach, personal trainer, or clinician.

In some examples, it may be desirable to use the garment according to aspects of the present disclosure to monitor users undergoing physically intensive activity while in an athletic or work environment. It may be desirable to use the light source to emit light having a property that indicates the amount of time the user has spent in different heart-rate zones. This may be desirable to indicate to the user or other person such as a supervisor, coach, personal trainer, or clinician the amount of time the user as spent in different hear-rate zones.

For example, if the user remains in heart rates zones 1 and 2 the light source 103 may be arranged emit light having first property (e.g. green light) to indicate that the user is undergoing safe activity.

If the user spends a continuous period of between 30 and 45 minutes in heart rate zone 3 the light source may emit light having second property (e.g. amber light) to indicate that the user's activity should be monitored. If the user spends a continuous period of more than 45 minutes in heart rate zone 3 then the light source may emit light having third property (e.g. red light) to indicate that the user is fatigued.

If the user spends a continuous period of between 2 and 4 minutes in heart rate zone 4 the light source may emit light having second property (e.g. amber light) to indicate that the user's activity should be monitored. If the user spends a continuous period of more than 4 minutes in heart rate zone 4 then the light source may emit light having third property (e.g. red light) to indicate that the user is fatigued.

If the user spends a continuous period of between 0.5 and 1 minute in heart rate zone 5 the light source may emit light having second property (e.g. amber light) to indicate that the user's activity should be monitored. If the user spends a continuous period of more than 1 minutes in heart rate zone 5 then the light source may emit light having third property (e.g. red light) to indicate that the user is fatigued.

It will be appreciated that these ranges are just examples. The skilled person will appreciate that any desired range may be set based on factors such as the type of activity and the fitness of the user.

In some examples, it may be desirable to determine the heart rate recovery for a user wearing the garment 200. Heart Rate Recovery is a useful measure of fitness and, longitudinally, can also be an indicator of training fatigue. Heart rate recovery is measured as the difference between the heart rate immediately at the end of a period of exercise and the heart rate 1 minute after the cessation of exercise. Generally, the fitter the individual, the greater the drop between exercising heart rate and the heart rate one minute after cessation of exercise. Typically, the drop is measured after exercising for at least three minutes at 60-80% of theoretical maximum heartrate. In some examples, a concerning score will be a less than 12 bpm drop, a good score will be between a 25-30 bpm drop and an excellent score will be between a 50-60 bpm drop. Of course, other numerical ranges are within the scope of the present disclosure. The light source 103 can emit light having a first property (e.g. green light) when the user has the excellent score, light having a second property (e.g. amber light) when the user has a good score, and light having a third property (e.g. red light) when the user has a concerning score.

In some examples, the light source 103 may emit light to indicate whether the user is at risk of injury. Light having a first property (e.g. green light) may indicate that the user is not at risk of injury. Light having a second property (e.g. amber light) may indicate that the user should be monitored. Light having a third property (e.g. red light) may indicate that the user is at risk of injury. The risk of injury may be derived from heart rate data by assessing the amount of time an individual spends in heart rate zones.

In some examples, the light source 103 may emit light based on the orthostatic heart rate of the user. The orthostatic heart rate can be used to analyse an individual's training readiness. It measures the difference between their resting heart rate and their standing heart rate. In an example operation for determining the orthostatic heart rate, a user may first lie down and rest for a period of time. Typically, the period of time is at least three minutes. The heart rate of the user is recorded during this time. The user then stands up and the heart rate may be measured shortly after standing (peak heart rate) or several minutes after standing (stabilised heart rate) or both peak and stabilised heart rate may be measured. The difference between the standing and the prone heart rate is determined so as to obtain the orthostatic heart rate.

In example operation, the light source 103 may output light having a first property (e.g. green light) when the difference between the lying and standing heart rate is within an allowable range indicating that the user is rested. The allowable range may be between 5 and 9 beats per minute, bpm. The light source 103 may output light having a second property (e.g. amber light) when the difference between the lying and standing heart rate is outside of the allowable range but within a predetermined distance of the allowable range. The light source 103 may output light having the second property when the difference is between 10 and 30 bpm. The output light having the second property will indicate that the user is under recovered and should lighten their training load. The light source 103 may output light having a third property (e.g. red light) when the difference between the lying and standing heart rate is outside of the allowable range and more than the predetermined distance from the allowable range. The light source 103 may output light having the third property when the difference is less than 5 bpm or more than 30 bpm. The output light having the third property will indicate that the user should seek medical evaluation and not undertake exercise.

A similar measure of over-training or under-recovery can be obtained by looking for variances in the Average Standing HR—Standing HR. If the variance was greater than 10-15 beats per minute, it may be deemed to be a sign of over-training. If there is a gradual increase in the variance over time, it suggests that the athlete was heading towards over-training. In an example operation, a user may lie down and rest for a period of time (e.g. 10 minutes). The user may then stand up and record the heart rate shortly thereafter (e.g. 12 seconds after standing up). At a later time (e.g. 90 seconds after standing up) the user may record their heart rate again. The difference between the first and second standing heart rates given an indication of whether the user is overtrained.

In example operation, the light source 103 may output light having a first property (e.g. green light) when the difference between the first and second standing heart rates is within an allowable range indicating that the user is rested. The allowable range may be less than 5 beats per minute, bpm. The light source 103 may output light having a second property (e.g. amber light) when the difference between the first and second standing heart rates is outside of the allowable range but within a predetermined distance of the allowable range. The light source 103 may output light having the second property when the difference is between 5 and 10 bpm. The output light having the second property will indicate that the user is possibly over-trained and should be monitored. The light source 103 may output light having a third property (e.g. red light) when the difference between the first and second standing heart rates is outside of the allowable range and more than the predetermined distance from the allowable range. The light source 103 may output light having the third property when the difference is more than 10 bpm. The output light having the third property will indicate that the user is over-trained and should undertake a lighter training load.

The light source 103 may emit light based on the core temperature of the user. The core temperature may be measured by temperature sensors incorporated into the electronics module 100 and/or the garment 200. Alternatively, the core temperature may be estimated based on the variation in heart rate as measured by heart rate sensors. An example approach for estimating core temperature from the heart rate is the Buller algorithm as disclosed in Buller, Mark & Tharion, William & Cheuvront, Samuel & Montain, Scott & Kenefick, Robert & Castellani, John & Latzka, William & Roberts, Warren & Richter, Mark & Jenkins, Odest & Hoyt, Reed. (2013). Estimation of human core temperature from sequential heart rate observations. Physiological measurement. 34. 781-798. 10.1088/0967-3334/34/7/781. The disclosures of which are hereby incorporated by reference.

In an example use case, the light source 103 may emit light having a first property (e.g. green light) when the user's core body temperature is determined to be within a safe range. The safe range may be between 36.5 degrees Celsius and 37.5 degrees Celsius, for example. The light source 103 may emit light having a second property (e.g. amber light) when the user's core body temperature is outside of the safe range but within 0.5 degrees Celsius of the safe range. For example, light having the second property may be emitted when the user's core body temperature is between 36 degrees Celsius and 36.5 degrees Celsius or between 37.5 degrees Celsius and 38 degrees Celsius. The light having the second property indicates to the user or other observer that the user can continue their activity but needs to be monitored closely. The light source 103 may emit light having the third property (e.g. red light) when the user's core body temperature is less than 36 degrees Celsius or greater than 38 degrees Celsius. The light having the third property indicates to the user or other observer that the user should stop their exercise and potentially seek medical attention. Of course, these numerical ranges are just examples and other ranges may be set as appropriate by the skilled person.

The light source 103 may emit light based on hydration level of the user. The hydration level may be determined from hydration sensors or may be estimated based on factors such as heart rate and core body temperature. The light source may emit light having different properties to indicate whether hydration level is safe, needs to be monitored, or a cause for concern.

The present disclosure is not limited to these examples. Any or a combination of these examples may be used. In addition or separately, the light source 103 103 may emit light to indicate the user's exercise readiness, whether they are due a rest period or need to seek medical attention, or whether the posture of the user is correct, needs monitoring or is a cause for concern.

Figure 3:
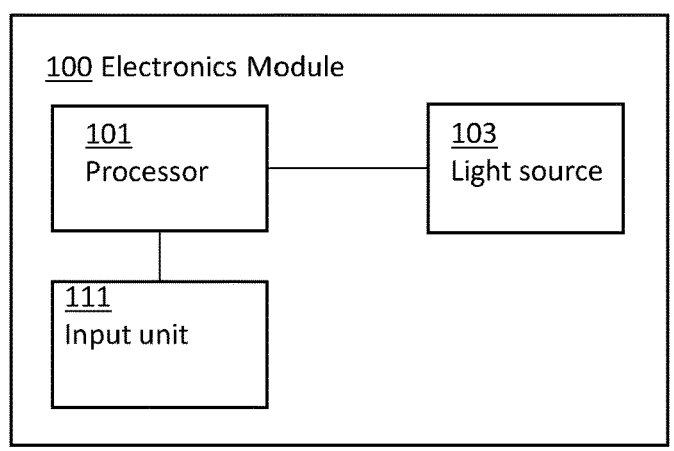
FIG. 3 shows another example electronics module according to aspects of the present disclosure.

Referring to FIG. 3, there is shown a simplified schematic diagram of another example electronics module 100 according to aspects of the present disclosure. The electronics module 100 comprises the processor 101 and the light source 103 of FIG. 2. The electronics module 100 further comprises an input unit 111. The input unit 111 is configured to receive a user input for selecting an operational mode. The processor 101 is configured to process the signals received from the sensing component so as to determine whether the activity of the user is within a predetermined allowable range for the selected operational mode. The operational modes may comprise different exercise modes (e.g. low intensity exercise, medium intensity exercise or high intensity exercise) these different exercise modes may be associated with different desired heart rate zones. The operational modes may comprise different activities such as walking, running, swimming, weight lifting and cycling which may be associated with different desired activity levels, postures, heart rate zones, etc. The present disclosure is not limited to any particular operational modes.

In some examples, the input unit 111 comprises a sensor 111 arranged to detect an object (such as the mobile device 300 of FIG. 1) being brought into the electronics module 100. In particular, the sensor 111 is a motion sensor that is arranged to detect a displacement of the electronics module 100 caused by the object being brought into proximity with the electronics module 100. These displacements of the electronics module 100 may be caused by the object being tapped against the electronics module 100. Physical contact between the object and the electronics module 100 is not required as the electronics module 100 may be in a pocket of a wearable article. This means that there may be a fabric barrier between the electronics module 100 and the object. In any event, the electronics module 100 being brought into contact with the fabric of the pocket will cause an impulse to be applied to the electronics module 100 which will be sensed by the sensor 111.

The sensor 111 may an inertial measurement unit. The inertial measurement unit may comprise an accelerometer and optionally one or both of a gyroscope and a magnetometer. A gyroscope/magnetometer is not required in all examples, and instead only an accelerometer may be provided or a gyroscope/magnetometer may be present but put into a low power state. A processor of the sensor 111 may perform processing tasks to classify different types of detected motion. The processor of the sensor 111 may in particular perform machine-learning functions so as to perform this classification. Performing the processing operations on the sensor 111 rather than the processor 101 is beneficial as it reduces power consumption, and leaves processor 101 free to perform other tasks. In addition, it allows for motion events to be detected even when the processor 101 is operating in a low power mode. The sensor 111 communicates with the processor 101 over a serial protocol such as the Serial Peripheral Interface (SPI), Inter-Integrated Circuit (I2C), Controller Area Network (CAN), and Recommended Standard 232 (RS-232). Other serial protocols are within the scope of the present disclosure. The sensor 111 is also able to send interrupt signals to the processor 101 when required so as to transition the processor 101 from a low power model to a normal power mode when a motion event is detected. The interrupt signals may be transmitted via one or more dedicated interrupt pins.

The sensor 111 may not just be used for cycling between different operational modes. The sensor 111 may also be used in determining whether the user is within the predetermined allowable range. This is particularly the case for motion sensors which can be used for motion and posture analysis.

Figure 4:
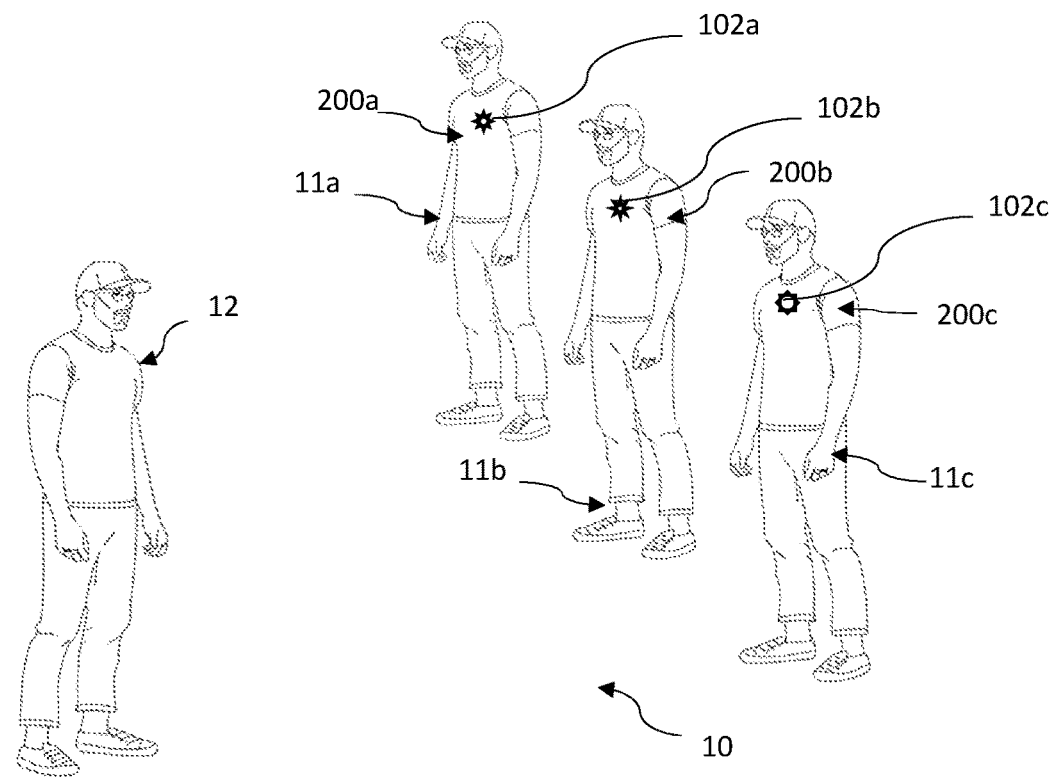
FIG. 4 shows another example system according to aspects of the present disclosure.

Referring to FIG. 4, there is shown another example system 10 according to aspects of the present disclosure. In this system 10 a plurality, three in this example, of garments 200*a*, 200*b*, 200*c* are provided. The garments 200*a*, 200*b*, 200*c* are each worn by a different user 11*a*, 11*b*, 11*c*. Electronics modules in accordance with the present disclosure are incorporated into the garments 200*a*, 200*b*, 200*c* and emit light 102*a*, 102*b*, 102*c* to indicate whether the activity of the user 11*a*, 11*b*, 11*c* wearing the garment 200*a*, 200*b*, 200*c* is within the predetermined allowable range. The garments 200*a*, 200*b*, 200*c* are constructed such that the emitted light 102*a*, 102*b*, 102*c* is visible from the outside surfaces of the garments 200*a*, 200*b*, 200*c*.

The users 11*a*, 11*b*, 11*c* are undergoing a training session and are being monitored by a coach 12. The coach 12 may want to quickly tell if the player if adhering to the training regime. For example, the coach 12 may want to quickly tell whether the users 11*a*, 11*b*, 11*c*, are operating in the correct heart rate zone or have the correct posture. The emitted light 102*a*, 102*b*, 102*c* from the electronics modules enables the coach to obtain this information. A separate mobile device, display etc. is not required. Advantageously, the present disclosure enables many users to be monitored at the same time in an easy and intuitive way. This approach is generally more user friendly than the using a separate mobile device and enables more users to be monitored at the same time. This is because mobile devices are only generally able to connect to a small number of devices over communication protocols such as Bluetooth®. Bluetooth is generally limited to 8 peripherals normally and most mobile phones only permit up to 5 connections. Moreover, the aspects of the present disclosure enable a user to monitor their own performance without the user of a separate mobile device. The user may look down at their garment to view the emitted light or observe themselves in a mirror.

Figure 5:
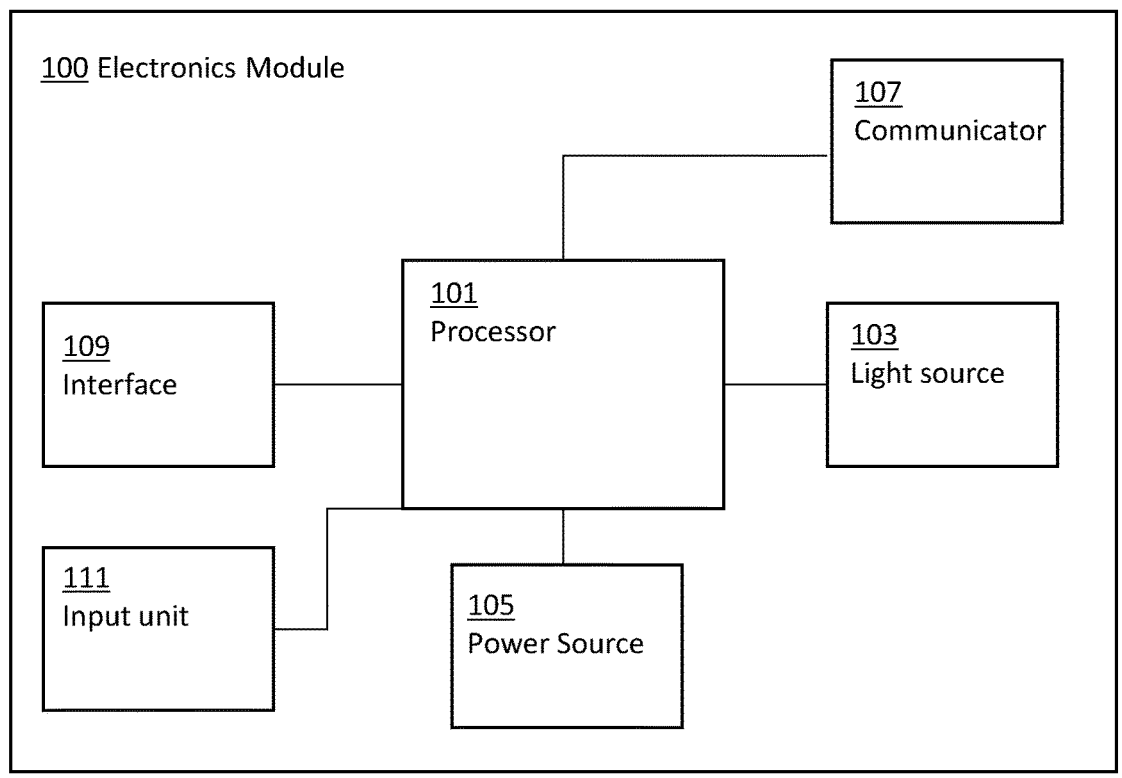
FIG. 5 shows a schematic diagram for yet another example electronics module according to aspects of the present disclosure.

Referring to FIG. 5, there is shown a schematic diagram of another example electronics module 100. The electronics module 100 comprises the processor 101, the light source 103 and the input unit 111 of FIGS. 2 and 3. This example electronics module 100 additionally comprises a power source 105, a communicator 107, and an interface 109. The electronics module 100 of the present disclosure are not limited to this particular construction and may not comprise all of these components. In addition, the electronics module 100 may comprise alternative or additional components.

The power source 105 is coupled to the processor 101 and is arranged to supply power to the processor 101. The power source 105 may comprise a plurality of power sources. The power source 105 may be a battery. The battery may be a rechargeable battery. The battery may be a rechargeable battery adapted to be charged wirelessly such as by inductive charging. The power source 105 may comprise an energy harvesting device. The energy harvesting device may be configured to generate electric power signals in response to kinetic events such as kinetic events performed by a wearer of the garment. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the garment. The energy harvesting device may be a thermoelectric energy harvesting device. The power source may be a super capacitor, or an energy cell.

The communicator 107 may be a mobile/cellular communicator operable to communicate the data wirelessly via one or more base stations. The communicator 107 may provide wireless communication capabilities for the garment and enables the garment to communicate via one or more wireless communication protocols such as used for communication over: a wireless wide area network (WWAN), a wireless metroarea network (WMAN), a wireless local area network (WLAN), a wireless personal area network (WPAN), Bluetooth® Low Energy, Bluetooth® Mesh, Bluetooth® 5, Thread, Zigbee, IEEE 802.15.4, Ant, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communicators may be provided for communicating over a combination of different communication protocols.

The electronics module 100 may comprise a Universal Integrated Circuit Card (UICC) that enables the electronics module 100 to access services provided by a mobile network operator (MNO) or virtual mobile network operator (VMNO). The UICC may include at least a read-only memory (ROM) configured to store an MNO/VMNO profile that the wearable article can utilize to register and interact with an MNO/VMNO. The UICC may be in the form of a Subscriber Identity Module (SIM) card. The electronics module 100 may have a receiving section arranged to receive the SIM card. In other examples, the UICC is embedded directly into a controller of the electronics module 100. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to electronics modules 100. The electronics modules 100 may comprise a secure element that represents an embedded Universal Integrated Circuit Card (eUICC).

The interface 109 is arranged to communicatively couple with a sensing component of the garment 200 (FIG. 1) so as to receive a signal from the sensing component. The processor 101 is communicatively coupled to the interface 109 and is arranged to receive the signals from the interface 109. The interface 109 may form a conductive coupling or a wireless (e.g. inductive) communication coupling with the electronics components of the garment 200.

The electronics module 100 is mounted on a garment 200 (FIG. 1) and conductively connected to sensing components such as electrodes of the garment via electrically conductive pathways of the garment 200. In a particular example, the sensing components are electrodes used to measure electro potential signals such as electrocardiogram (ECG) signals.

The processor 101 may be a component of a controller such as a microcontroller. The controller may have an integral communicator such as a Bluetooth® antenna. The controller may have an internal memory and may also be communicatively connected to an external memory of the electronics module such as a NAND Flash memory. The memory is used to for the storage of data when no wireless connection is available between the electronics module 100 a mobile device 300 (FIG. 1). The memory may have a storage capacity of at least 1 GB and preferably at least 2 GB. The processor 101 is connected to an interface 109 via an analog-to-digital converter (ADC) fronted end and an electrostatic discharge (ESD) protection circuit. The ADC fronted end converts the raw analog signal received from sensing components of the garment 200 into a digital signal. The ADC frontend may also perform filtering operations on the received signals.

Figure 6:
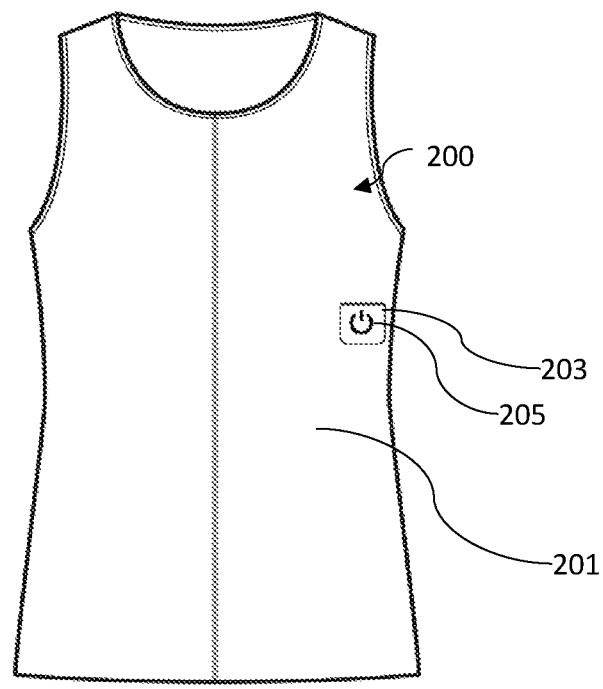
FIG. 6 shows an example wearable article according to aspects of the present disclosure.

Referring to FIG. 6, there is shown an example garment 200 according to aspects of the present disclosure. The garment 200 comprises an electronics module holder 203 provided on an outside surface 201 of the garment 200. The electronics module holder 203 is arranged to hold the electronics module according to aspects of the present disclosure. A visual symbol 205 is provided on the outside surface of the electronics module holder 203.

Figure 7:
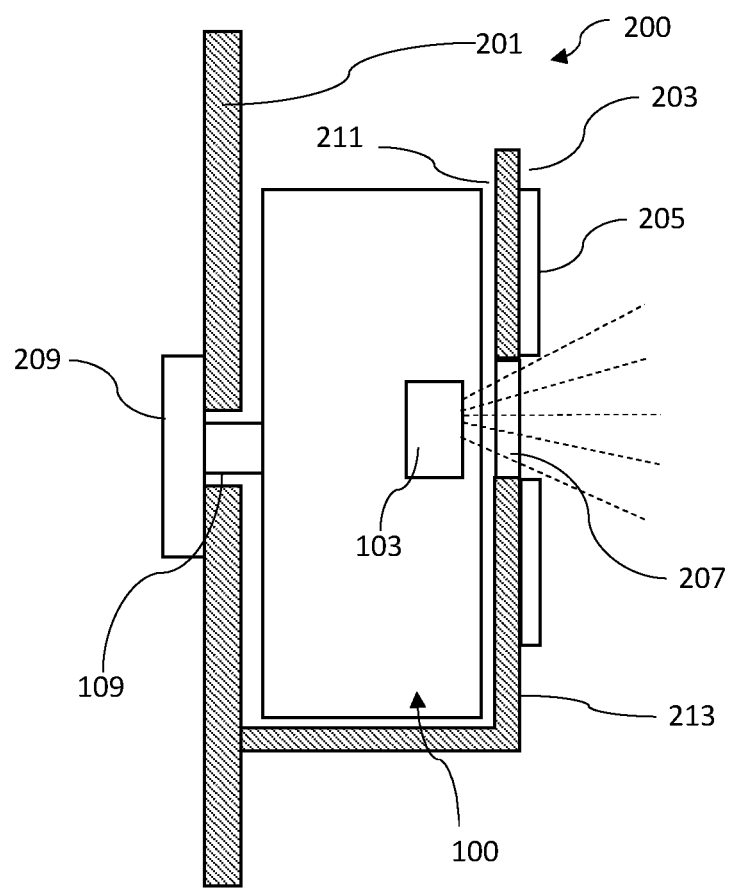
FIG. 7 shows a sectional view of a wearable article comprising an electronics module.

Referring to FIG. 7, there is shown a sectional view of a garment 200 comprising an electronics module 100 disposed within the electronics module holder 203 of the garment 200. A terminal region 209 is provided on the inside surface of the garment 200. The terminal region 209 connects to sensing components of the garment 200 via one or more electrically conductive pathways.

The electronics module holder 203 in this example is a pocket 203 provided on the outside surface of the garment 200. The electronics module holder 203 comprises a layer of material 203 which is bonded, stitched, otherwise attached to or integrally formed with the garment 200. The electronics module holder 203 has an inner surface 211 facing the electronics module 100. The electronics module holder 203 has an outer surface 213 which can be considered as part of the outer surface 201, 213 of the garment 200.

The garment 200 is constructed such that light emitted by the light source 103 of the electronics module 100 is visible from the outside surface of the garment 200. In this example, the garment 200 comprises an opening 207 provided in the layer of material 203 of the electronics module holder 203. The opening 207 extends from the inner surface 211 to the outer surface 213. The opening 207 is positioned such that, when the electronics module 100 is provided in the electronics module holder 203, the light source 103 is aligned with the opening 207. The opening 207 may be formed by removing material from the layer of material 203 of the electronics module holder 203 or the layer of material 203 may be formed to include the opening 206 during manufacture.

Rather than providing an opening 207 in the material of the garment 200, a window may instead be provided. The window may be constructed from a transparent, translucent, or light diffracting material. The use of a light diffracting material may provide a light pipe effect to help the light source 103 appear bigger than they are. In other examples, the material of the electronics module holder 203 may have an open-cell construction in the vicinity of the light source 103, when positioned in the electronics module holder 203, such that the light source 103 is visible from the outside of the garment 200.

A visual marker 205 is provided on the outside surface 213 of the electronics module holder 203. The visual marker 205 is constructed in this example to take into account the presence of the opening 207.

Figure 8:
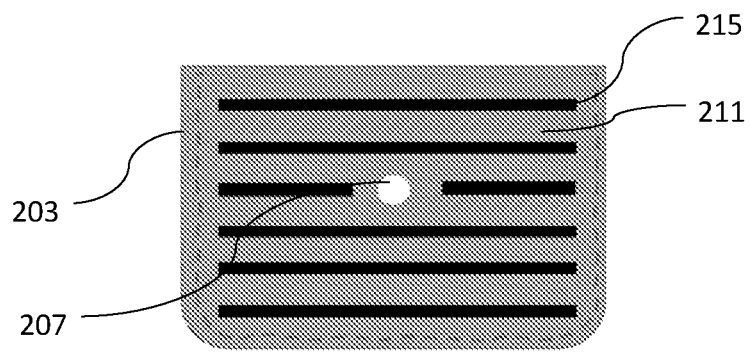
FIG. 8 shows the inner surface of an example electronics module holder of a wearable article according to aspects of the present disclosure.

Referring to FIG. 8, there is shown an example outer layer 203 of electronics module holder 203 in FIG. 7. The outer layer 203 is bonded, stitched, or otherwise attached to the garment 200. The outer layer 203 may also be integrally formed with the garment 200. FIG. 8 shows the inner surface 211 of the outer layer 203. The inner surface 211 is provided with a surface 215 which increases friction between the inner surface 211 and the electronics module 100 when positioned in the electronics module holder 203. The surface 215 comprises a number (six in this example) of horizontal lines of gripping material provided on the inner surface 211. The gripping material is a silicone-based coating. The surface 215 helps reduce unnecessary rotational or translational movement of the electronics module 100 when positioned in the electronics module holder 203 and helps maintain the interface 109 (FIG. 7) of the electronics module 100 in contact with the terminal region 209.

Figure 9:
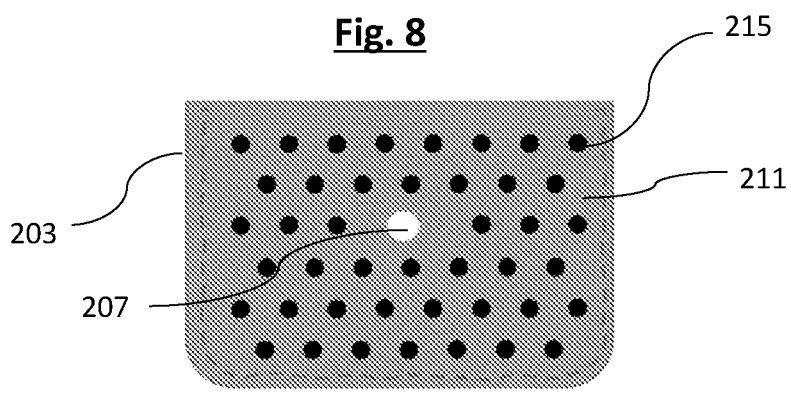
FIG. 9 shows the inner surface of another example electronics module holder of a wearable article according to aspects of the present disclosure.

Referring to FIG. 9, there is shown another example of the inner surface 211 of the electronics module holder 203. In this example, the surface 215 comprises a number of dots of gripping material provided on the inner surface 211. The gripping material is a silicone-based coating.

It will be appreciated that FIGS. 8 and 9 are only two examples of surfaces 215 used to increase friction between the electronics module holder 203 and the electronics module 100. In other examples, the electronics module holder 203 may be separately or additionally elasticised to help hold the electronics module 100 in place. Additionally or separately, the electronics module 100 may be provided with a surface which increases friction between the garment 200 and the electronics module 100 so as to limit motion of the electronics module 100 relative to the garment 200. The surface of the electronics module 100 may comprises a rubberised grip texture, for example.

Figure 10:
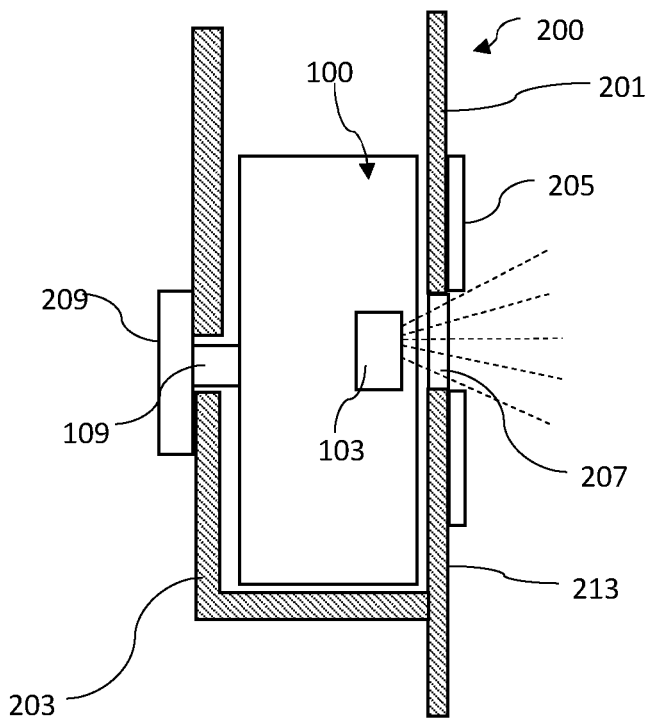
FIG. 10 shows a sectional view of another example wearable article comprising an electronics module according to aspects of the present disclosure.

Referring to FIG. 10, there is shown another example sectional view of a garment 200 comprising an electronics module 100 disposed within the electronics module holder 203 of the garment 200. The electronics module holder 203 in this example is a pocket 203 provided on the inside surface of the garment 200. The garment 200 is constructed such that light emitted by the light source 103 of the electronics module 100 is visible from the outside surface of the garment 200. In this example, the garment 200 comprises an opening 207 extending through the outside surface 201 of the garment 200. The opening 207 is positioned such that, when the electronics module 100 is provided in the electronics module holder 203, the light source 103 is aligned with the opening 207. A visual marker 205 is provided on the outside surface 201 of the garment 200. The visual marker 205 is constructed in this example to take into account the presence of the opening 207. The other features of the garment may be the same as or similar to those of FIGS. 7 to 9.

In FIGS. 6 to 10, the garment 200 comprises a visual maker 205 located on the outside surface of the garment 200. The visual marker 205 is located at a position corresponding to the electronics module holder 203. The visual marker 205 indicates the location of the electronics module 100 when located in the electronics module holder 203.

The visual maker 205 helps a user activate and/or control the operation of the electronics module 100. When positioned in the electronics module holder 203, the electronics module 100 may be concealed or not easily visible or discernible to the user. This will particularly be the case if the garment 200 has a number of padded areas to help conceal the visual appearance of the electronics module 100 when positioned in the electronics module holder 203. Concealing the appearance of the electronics module 100 is desirable so as to make the garment 200 look more visually attractive to the user as well as fell more comfortable to wear.

Beneficially, the visual marker 205 is placed on the exterior face of the garment 200 and is visible to the user. The visual marker 205 is aligned with the electronics module 100 when positioned in the electronics module holder 203. The visual marker 205 therefore indicates the location of the electronics module 100 when located in the electronics module holder 203.

In some example, the electronics module 100 has an input unit 111 (FIG. 3) for controlling the operation of the electronics module 100. The input unit 111 may be a tactile button or a motion sensor amongst other examples. The input unit 111 may in particular require an object such as the hand of the user to approach and tap against the electronics module 100 to perform a control operation. This tapping operation may be performed on the outer surface of the garment 200 and sensed through one or more layers of fabric by the input unit 111. The visual marker 205 in accordance with aspects of the present disclosure indicates the location of the input unit 111 such that an object tapping on the garment 200 in the vicinity of the visual marker 205 is detectable by the input unit 111 of the electronics module 100.

Beneficially, the visual marker 205 allows the user to quickly and easily see where to tap the electronics module 100. This makes it easier for the user to control the operation of the electronics module 100 while positioned in the electronics module holder 203.

In some examples, the electronics module 100 may comprise an antenna coil such as a near field communication (NFC) coil which is used to exchange information with a mobile device 300 (FIG. 1). This may in particular be for use in tap-to-pair operations so as to pair the electronics module 100 and the mobile device 300 over another communication protocol such as, but not limited to, Bluetooth®. The visual maker 205 can beneficially additionally or separately indicate the location of the antenna coil. This enables the user to quickly and easily see where to tap their mobile device 300 so as to enable the data exchange to take place.

Figure 11:
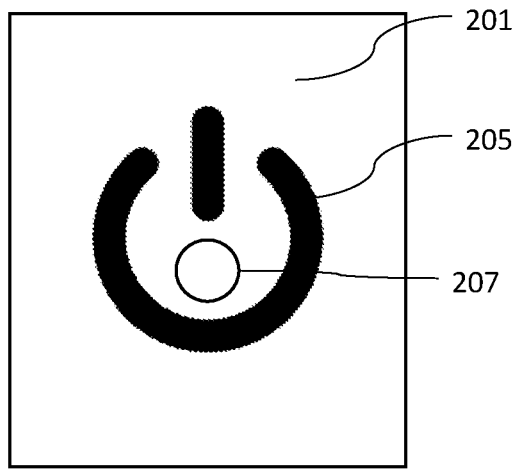
FIGS. 11 to 14 show examples of different visual markers according to aspects of the present disclosure.
Figure 12:
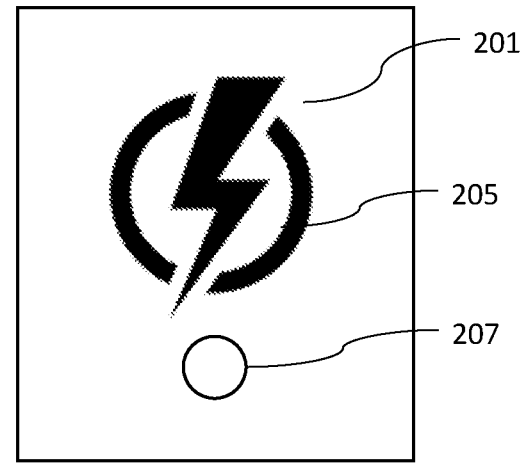
Figure 13:
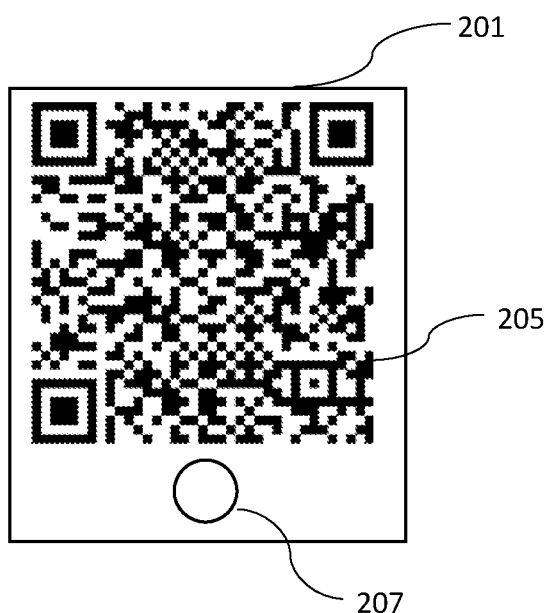
Figure 14:
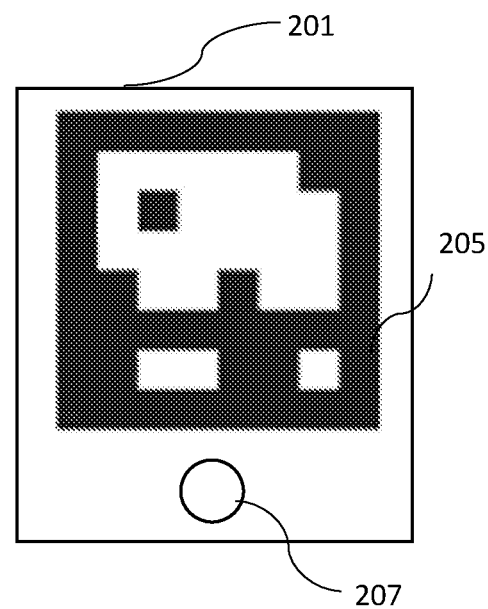

Referring to FIGS. 11 to 14, there are shown example outside surfaces 201 of garments 200 with different forms of visual marker 205 with openings 207 incorporated into or provided alongside the visual markers 205. FIGS. 11 and 12 show visual makers 205 in the form of simple icons that are easily understandable to users. FIGS. 13 and 14 show visual markers which comprise machine-readable code. The machine-readable code may comprise an identifier or other information that can be read by a machine. For example, the mobile device 300 may read the machine-readable code using a camera of the mobile device 300. This provides added functionality for the garment 200.

In some examples, the visual marker 205 may act as a fiducial marker 205. A fiducial marker 205 is useable as a point of reference for the garment 200 and thus enables the position of the garment 200 and the motion of the garment 200 over time to be monitored simply by capturing images of the garment 200. In this way, the motion of the wearer of the garment 200 is tracked by determining the location of the fiducial marker 205 in the captured image. The fiducial marker 205 may be in the form of a 2D image. The fiducial marker 205 of the present invention is beneficial as it is simple, of low cost and does not negatively affect the comfort of the garment for the wearer. The fiducial marker may be an augmented reality (AR) marker.

In the example of FIG. 13, the marker 205 is a Quick-Response (QR) code and comprises a visual symbol in the form of black marks upon white pathways. The black marks represent the characters in the code string. The visual symbol may additionally encode redundant information for error detection, correction, and uniqueness over different rotations of the marker.

In the example of FIG. 14, the marker 205 is based on an AR marker 205. The marker 205 comprises a visual symbol in the form of a 6×6 grid of black or white cells which represent 36 binary '0' or '1' symbols. The 36-bit sequence encodes the code string and may additionally encode redundant information for error detection, correction and uniqueness over the different rotations of the marker.

In both examples, the code string/data string may be retrieved from the marker 205 by processing an image containing the visual symbol. It will be appreciated that known image processing operations such as contour extraction and edge detection will be used to read the symbol from the image.

The visual marker 205 may be integrated into the garment 200. The visual marker 205 may be printed onto or into the garment 200. Any known garment printing technique may be used such as screen printing or inkjet printing. The visual marker 205 may be embroidered onto the garment 200.

The visual maker 205 is not limited to the examples described above.

Figure 15:
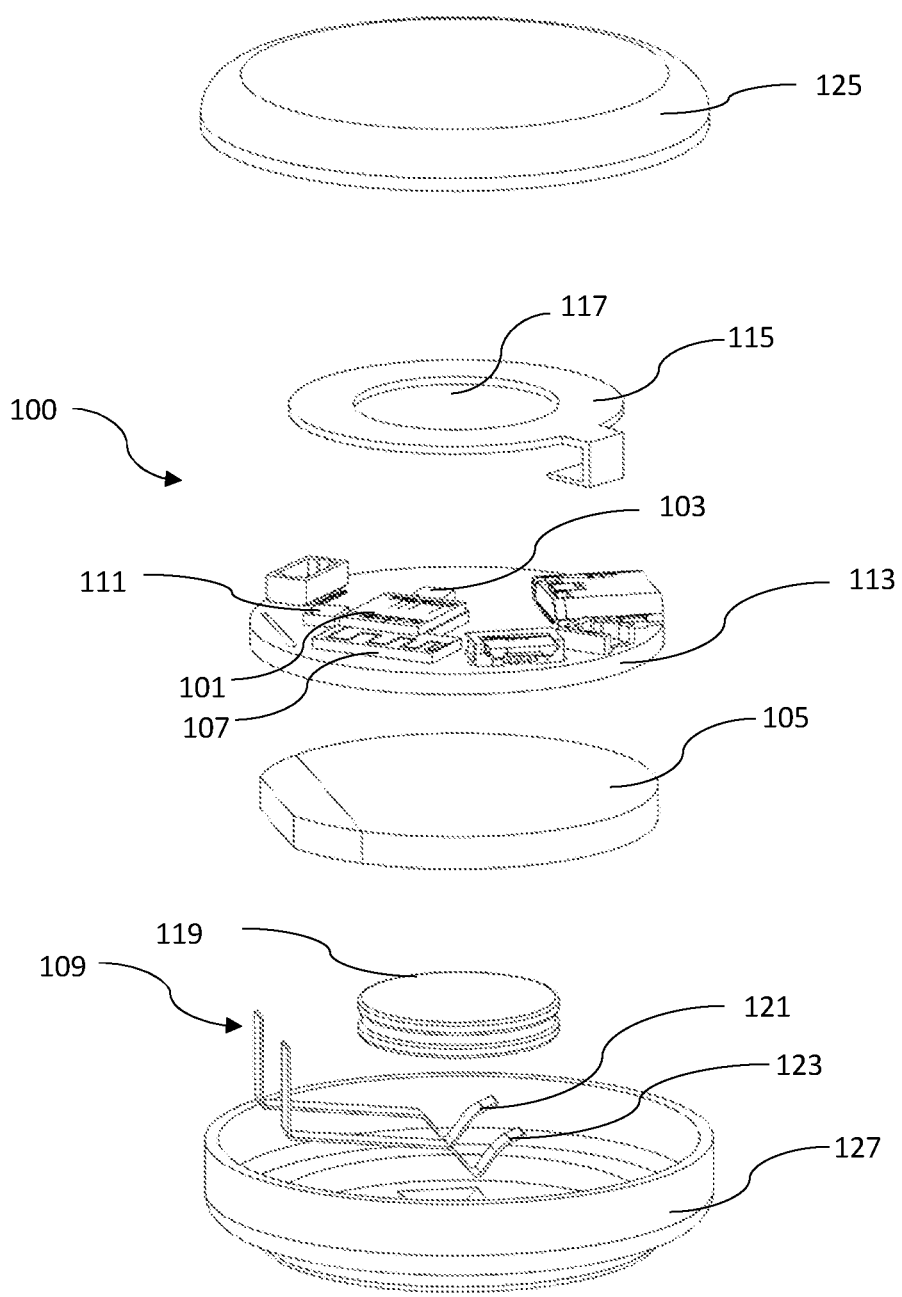
FIG. 15 shows an exploded view of yet another electronics module according to aspects of the present disclosure.

Referring to FIG. 15, there is shown an exploded view of an example electronics module 100 according to aspects of the present disclosure.

The electronics module 100 comprises the processor 101, light source 103, first communicator 107 and input unit 111 provided on a printed circuit board 113. The power source 105 is provided separately and below the printed circuit board 113. A second communicator 115 in the form of an NFC antenna 115 is also provided. The NFC antenna 115 is positioned above the printed circuit board 113 and comprises an aperture 117 such that the NFC antenna 115 does not obscure light emitted by the light source 103. The electronics module 100 further comprises the interface 109. The interface 109 comprises a magnet 113, and two conductive prongs 115, 117.

The components of the electronics module 100 are provided within a housing formed of a top enclosure 125 and a bottom enclosure 127. The NFC antenna 115 is provided proximate to the top enclosure 125. The bottom enclosure 127 is closest to the body of the wearer in use and the top enclosure 125 is furthest away from the body of the wearer in use. Beneficially, providing the NFC antenna 115 proximate to the top enclosure 125 minimises the communication distance between the NFC antenna 115 and the mobile device 300.

Figure 16:
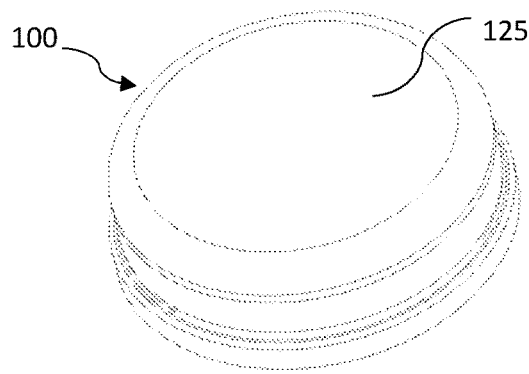
FIGS. 16 and 17 show perspective views of the electronics module of FIG. 15.
Figure 17:
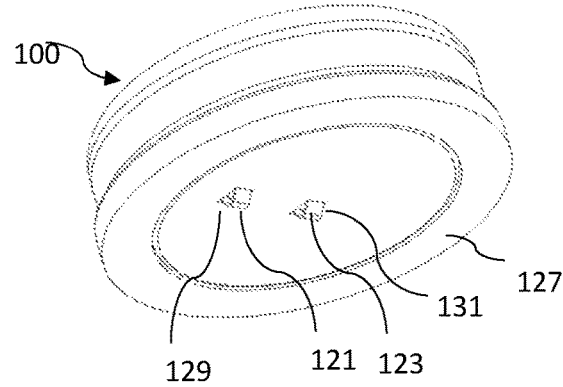

Referring to FIGS. 16 and 17, there is shown an electronics module 100 according to aspects of the present disclosure. The electronics module 100 may be the same as any of the electronics modules 100 as described above in relation to FIGS. 1 to 15. The electronics module 100 comprises a housing which contains the components of the electronics module 100. The housing comprises a top enclosure 125 and a bottom enclosure 127. The bottom enclosure 127 is closest to the body of the wearer in use and the top enclosure 125 is furthest away from the body of the wearer in use. First and second conductive prongs 121, 123 extend from openings 129, 131 in the bottom enclosure 127. The first and second conductive prongs 121, 123 are able to electrically conductively connect with conductive elements provided on a textile so as to electrically conductively connect the electronics module 100 to the conductive elements of the textile. The use of conductive prongs 121, 123 to electrically conductively connect the electronics module 100 to the textile are not required in all aspects of the present disclosure. Other forms of conductive connection may be provided such as via conductive studs or pins. In addition, a conductive connection may not be required as a wireless communication connection may be formed between the electronics module 100 and electronics components of the textile to allow for data exchange between the electronics module 100 and the electronics components of the textile. In one example, the electronics module 100 comprises an NFC coil proximate to the bottom enclosure 127 and the textile material comprises a corresponding NFC coil These NFC coils form a communicative coupling when the electronics module 100 is brought into proximity with the textile to allow for data exchange.

Figure 18:
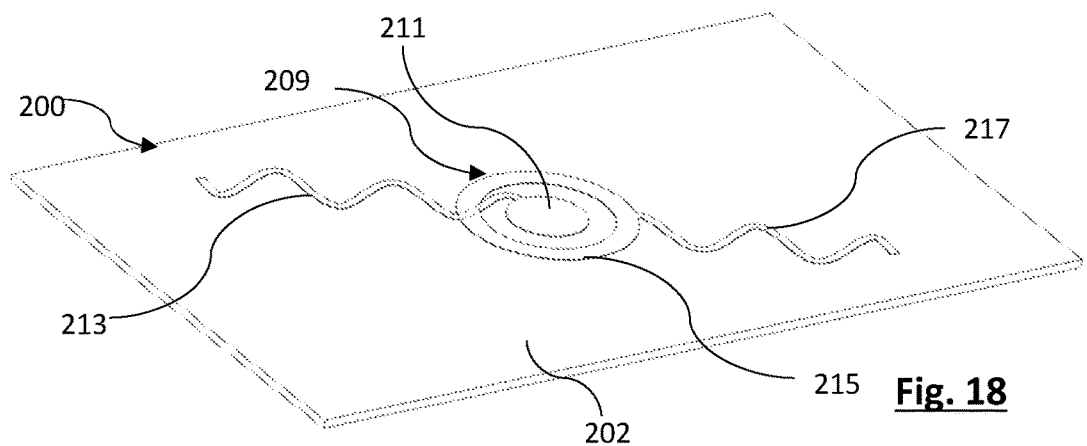
FIG. 18 shows a perspective view of a component of a garment according to aspects of the present disclosure.

Referring to FIG. 18, there is shown an example textile layer of a garment 200 according to aspects of the present disclosure. The garment 200 comprises a textile material 202 and conductive elements 211, 213, 215, 217 provided on the textile material 202. The conductive elements 211, 213, 215, 217 comprise the terminal region 209 of FIGS. 7 and 10. The terminal region 209 comprises a first terminal 211. A first electrically conductive pathway 213 extends from the first terminal 211 to a first electrode (not shown). The first electrically conductive pathway 213 therefore electrically connects the first terminal 211 to the first electrode. The conductive elements 211, 213, 215, 217 further comprise a second terminal 215 and a second electrically conductive pathway 217 that extends from the second terminal 215 to a second electrode (not shown). The second electrically conductive pathway 217 therefore electrically connects the second terminal 215 to the second electrode. The first and second terminals 211, 215 are arranged as concentric circles. A portion of the first electrically conductive pathway 213 extends under the second terminal 215. An insulating layer (not shown) insulates the first electrically conductive pathway 213 from the second terminal 215. This is just one example arranged of electrically conductive pathways on a textile. Other arrangements such as different positioning of electrically conductive pathways, and the use of different materials are within the scope of the present disclosure. For example, the electrically conductive pathways may be formed from a conductive thread or wire. The electrically conductive pathway may be incorporated into the textile. The electrically conductive pathway may be an electrically conductive track or film. The electrically conductive pathway may be a conductive transfer. The conductive material may be formed from a fibre or yarn of the textile. This may mean that an electrically conductive materials are incorporated into the fibre/yarn. In some examples, the conductive pathways may be provided on the underside surface of the textile. In some examples, an aperture may be provided in the textile so as to allow the electronics module to conductively connect to the conductive pathways.

Figure 19:
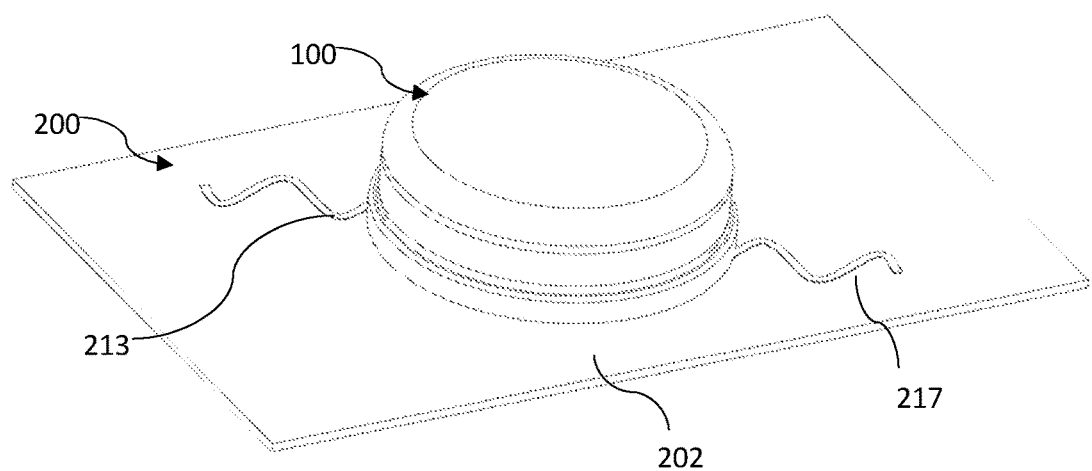
FIG. 19 shows a perspective view of the electronics module of FIGS. 16 and 17 mounted on the garment of FIG. 18.

Referring to FIG. 19, there is shown the electronics module 100 of FIGS. 16 and 17 attached to the garment 200 of FIG. 18. The first conductive prong 121 is brought into conductive electrical contact with the first terminal 211 and the second conductive prong 123 is brought into conductive electrical contact with the second terminal 215. A magnet (FIG. 15, element 119) may be provided in the electronics module 100 and on the underside of the garment 200 so as to maintain the electronics module 100 in releasable attachment with the garment 200.

Figure 20:
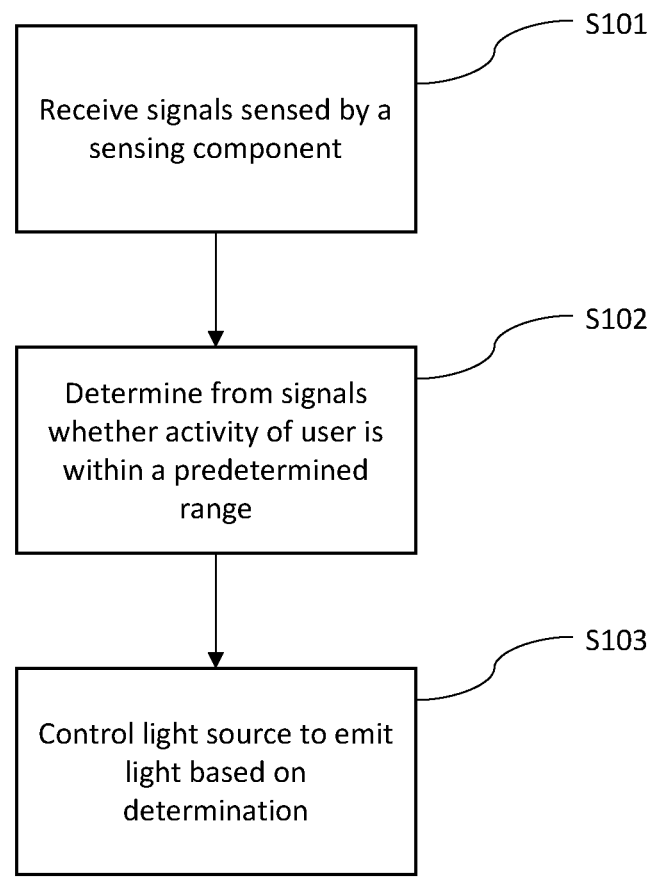
FIG. 20 shows a process flow diagram for an example method according to aspects of the present disclosure.

Referring to FIG. 20, there is shown a process flow diagram for an example method according to aspects of the present disclosure. The method is performed by an electronics module for a wearable article.

Step S101 of the method comprises receiving, by a processor of the electronics module, signals sensed by a sensing component, the signals relating to the activity of a user wearing the wearable article.

Step S102 of the method comprises processing, by the processor, the signals so as to determine whether the activity of the user is within a predetermined allowable range.

Step S103 of the method comprises controlling, by the processor, a light source of the electronics module to emit light based on the determination by the processor, wherein the emitted light is for indicating whether the activity of the user is within the predetermined allowable range.

In the present disclosure, the electronics module may also be referred to as an electronics device or unit. These terms may be used interchangeably.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA), programmable System on Chip (pSoC), or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others. All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wearable assembly comprising a wearable article and an electronics module arranged to be removably coupled to the wearable article,
    the wearable article comprising:
        an electronics module holder arranged to hold the electronics module;
        a first sensing component comprising an electrode for sensing signals relating to the cardiac activity of a user; and
        an electrically conductive pathway that extends from the first sensing component to the electronics module holder,
    the electronics module comprising:
        a second sensing component for sensing signals relating to the cardiac activity of a user;
        an interface element arranged to communicatively couple with the first sensing component of the wearable article so as to receive signals from the first sensing component of the wearable article;
        a processor configured to process signals sensed by the second sensing component of the electronics module or the signals sensed by the first sensing component of the wearable article, the signals relating to the cardiac activity of a user wearing the electronics module, the processor configured to process the signals so as to determine whether the cardiac activity of the user is within a predetermined allowable range;
        a light source configured to emit light based on the determination by the processor, wherein the emitted light is for indicating whether the cardiac activity of the user is within the predetermined allowable range; and
        a housing, wherein the processor and the light source are provided in the housing, and wherein the housing is constructed such that light emitted by the light source is visible from the outside surface of the housing,
    wherein the wearable article is a garment within which the electronics module is placed and light emitted by the light source is visible from the outside surface of the garment.

2. A wearable assembly according to claim 1, wherein the electronics module further comprises an input unit configured to receive a user input for selecting an operational mode, and wherein the processor is configured to process the signals so as to determine whether the cardiac activity of the user is within a predetermined allowable range for the selected operational mode.

3. A wearable assembly according to claim 2, wherein the input unit comprises a sensor arranged to detect an object being brought into proximity with the electronics arrangement.

4. A wearable assembly according to claim 3, wherein the sensor is a motion sensor.

5. A wearable assembly according to claim 4, wherein the motion sensor comprises an accelerometer.

6. A wearable assembly according to claim 4, wherein the processor is configured to process signals received from the motion sensor.

7. A wearable assembly according to claim 1, wherein the predetermined allowable range is a predetermined heart rate zone and wherein the light source is configured to emit light having a first property when the cardiac activity of the user is determined to be within the predetermined heart rate zone, the light source is configured to emit light having a second property when the cardiac activity of the user is determined to be outside of the predetermined heart rate zone but within a predetermined distance of the predetermined heart rate zone, and the light source is configured to emit light having a third property when the cardiac activity of the user is outside of the predetermined heart rate zone and more than the predetermined distance from the predetermined allowable range.

8. A wearable assembly according to claim 7, wherein the light source is configured to emit light having a first color when the cardiac activity of the user is determined to be within the predetermined heart rate zone, and the light source is configured to emit light having a color other than the first color when the cardiac activity of the user is determined to be outside of the predetermined heart rate zone.

9. A wearable assembly according to claim 8, wherein the first sensing component is used to measure electro potential signals.

10. A wearable assembly according to claim 1, wherein the wearable article comprises an opening positioned such that light emitted by the light source is visible from the outside surface of the wearable article.

11. A wearable assembly according to claim 10, wherein the wearable article comprises a window constructed from a transparent, translucent, or light-diffracting material.

12. A wearable assembly according to claim 1, wherein the interface element is arranged to receive analog signals from the first sensing component.

13. A wearable assembly according to claim 12, wherein the electronics module further comprises an analog-to-digital front-end arranged to covert the analog signals into digital signals, and wherein the processor is arranged to receive the digital signals from the analog-to-digital front-end.

14. A wearable assembly according to claim 1, wherein the electronics module holder comprising a mechanical interface arranged to mechanically couple the electronics module to the wearable article.

15. A wearable assembly according to claim 14, wherein the mechanical interface is configured to maintain the electronics module in a particular orientation with respect to the wearable article when the electronics module is coupled to the wearable article.

16. A wearable assembly according to claim 1, wherein the electronics module holder is provided on an inside surface of the wearable article or an outside surface of the wearable article.

17. A wearable assembly according to claim 1, wherein the housing comprises a first portion and a second portion, the second portion being closest to the body of the wearer in use and wherein the interface element extends from the second portion of the housing.

18. A wearable assembly according to claim 1, wherein the electronics module further comprises a communicator arranged to communicatively couple with an external device so as to send data to and/or receive data from the external device.

19. A wearable assembly according to claim 1, wherein the electronics module is provided with a surface which increases friction between the wearable article and the electronics module so as to limit motion of the electronics module relative to the wearable article.

20. A wearable assembly according to claim 1, further comprising a visual marker located on an outside surface of the wearable article, wherein the visual marker is located at a position corresponding to the electronics module holder, and optionally wherein the visual marker is configured to indicate the location of the electronics module when located in the electronics module holder, and optionally wherein the visual marker is configured to indicate the location of the input unit of the electronics module such that an object tapping on the wearable article in the vicinity of the visual marker is detectable by the input unit of the electronics module.

21. A wearable assembly according to claim 20, wherein the visual marker comprises a machine-readable code, optionally wherein the machine-readable code is a QR code.

* * * * *